United States Patent [19]

Grimm, III

[11] 3,957,964

[45] May 18, 1976

[54] DENTIFRICE CONTAINING ENCAPSULATED FLAVORING

[75] Inventor: John Edward Grimm, III, New York, N.Y.

[73] Assignee: Colgate-Palmolive Company, New York, N.Y.

[22] Filed: June 3, 1975

[21] Appl. No.: 583,380

Related U.S. Application Data

[63] Continuation of Ser. No. 438,028, Jan. 30, 1974, abandoned, which is a continuation of Ser. No. 235,038, March 15, 1972, abandoned.

[52] U.S. Cl. ............................. 424/10; 424/49; 426/533; 426/534
[51] Int. Cl.² ............................................ A61K 7/16
[58] Field of Search ............... 424/49, 10; 426/175, 426/221, 223

[56] References Cited

UNITED STATES PATENTS

| 2,004,957 | 6/1935 | Messner | 424/99 X |
|---|---|---|---|
| 2,778,045 | 1/1957 | Bly et al. | 424/49 X |
| 2,800,457 | 7/1957 | Green et al. | 252/522 X |
| 2,975,102 | 3/1961 | Matsumura et al. | 424/49 |
| 2,984,570 | 5/1961 | Prell | 99/148 |
| 2,991,229 | 7/1961 | Ivison | 424/49 |
| 3,137,631 | 6/1964 | Soloway | 252/522 X |
| 3,228,845 | 1/1966 | Najjar | 424/49 |
| 3,495,988 | 2/1970 | Balassa | 99/71 |
| 3,516,941 | 6/1970 | Matson | 252/522 X |
| 3,711,604 | 1/1973 | Colodney et al. | 424/52 |

*Primary Examiner*—Shep K. Rose
*Attorney, Agent, or Firm*—Steven J. Baron; Murray M. Grill; Herbert S. Sylvester

[57] ABSTRACT

A dentifrice which releases bursts of flavor during use and includes a minor proportion of an encapsulated flavoring material in a dentifrice. The encapsulated flavoring is maintained separate from the dentifrice base during storage but is released into it by breaking of the encapsulating shells or coating when the dentifrice is used.

19 Claims, No Drawings

DENTIFRICE CONTAINING ENCAPSULATED FLAVORING

This application is a continuation of application Ser. No. 438,028, filed on Jan. 30, 1974, now abandoned which is a continuation of application Ser. No. 235,038, filed on Mar. 15, 1972, now abandoned; the benefit of which filing dates are claimed.

This invention relates to flavored dentifrices in which flavoring material is encapsulated so as to maintain it substantially separate from at least some of the dentifice constituents during manufacture and storage but to allow release of the flavor into the dentifrice during normal use thereof. The invention also relates to the encapsulation of other dentrifice constituents with the flavoring material and to methods of producing the invented dentifrices.

Dentifrices normally comprise polishing agents and surface active or detergent materials. When such are brushed onto the teeth they help to remove bits of food lodged in crevices between the teeth and they also clean the surfaces of the teeth and gums of an agglutinative proteinaceous plaque thereon. Tooth powders, while excellent cleaners, have not been accepted by the public to the extent that toothpastes or dental creams have been. These latter products, whether dispensed from flexible or resilient tubes or from pressurized containers, such as "aerosol" dispensers, have been most widely approved by the public. Such pastes or creams will normally comprise polishing agent(s), vehicle(s), surface active agent(s) or detergent(s), gelling agent(s), and various other adjuvants, such as flavors, colorants, bactericides, tooth hardeners, e.g., fluorides or fluorine compounds, and preservatives or stabilizers.

Paste or cream dentifrices may be based on aqueous or substantially non-aqueous systems. The former will usually include substantial proportions of finely divided, solid polishing agent, surface active agent, gelling agent and some non-aqueous vehicle, e.g., glycerol, sorbitol, and will be opaque, whereas the latter type will often be a clear gel, containing a minor proportion of a visually clear particulate solid polishing agent, a larger proportion of non-aqueous vehicle, surface active agent and gelling agent, with a minor proportion of water often being prsent. It has been suggested that the properties of toothpastes, including the clear gels, may be modified by intentionally incorporating gas bubbles in them, to modify the density of the product and its viscosity and to make clear gels of a novel and attractive appearance.

Encapsulation of various materials has been utilized in recent years and in many cases microencapsulation has been successfully practiced. For example, "Carbon" papers and encapsulataed adhesives have been made. However, until the present invention dentifrices containing encapsulated flavorings were not known and their special advantages were not recognized.

With visually clear gel dentifrices the encapsulated flavorings, which may also be colored, give the product a distinctive appearance in addition to allowing the use of a wide variety of flavors which are more stable and "fresher" tasting when included in encapsulated form in the dentifrice. The flavors, which are released during the use of the dentifrice, by a brushing action or by crushing between the teeth or between the tongue and the roof of the mouth, generate bursts of flavor which are significantly preferred by the user to the lesser taste sensations obtainable when the entire flavoring content is evenly distributed throughout the dentifrice. Thus, lesser quantities of flavoring may be utilized when the flavor or flavors are encapsulated in the dentifrice. The "appearance" or disappearance of bursts of flavoring may be employed to mark the time at which the cleaning of the teeth may be considered to be finished. This is especially useful for timing the brushing of children's teeth and ensuring that the brushing was vigorous enough. Fluorides, antibiotics, bactericides and colorants which might not be as stable when distributed throughout the entire dentifrice composition may be used and released in active form when the dentifrice capsules are broken during brushing. Special color effects may be obtained by such releases of dyes or water dispersible pigments and color changes may be obtained as capsules of different wall thicknesses or sizes are sequentially broken. If a small proportion of colorant penetrates the capsule wall during storage a mottled or variegated coloring effect may be obtained on the dentifrice. Of course, by regulating capsule wall thicknesses and sizes, an even release of bursts of the same or different flavors and colors may be effected during use of the dentifrices. All these advantages are obtained at little extra expense and in some cases, as when lesser proportions of flavorings or other materials, more stable when encapsulated, may be used with equivalent effects, significant savings may be obtained.

In accordance with the present invention a dentifrice comprises a minor proportion of an encapsulated flavoring material, the capsule being a minor proportion of the dentifrice composition and including a flavoring material which is encapsulated or covered with a shell or coating through which the flavoring material preferably does not penetrate substantially during storage of the dentifrice but which shell or coating is broken during use of the dentifrice, causing release of the flavor. In more limited aspects of the invention, it is of a dentifrice paste, cream or gel which comprises certain percentages of vehicle(s), polishing agent(s), gelling agent(s), surface active agent(s) or synthetic organic or soap detergent(s) and encapsulated flavoring(s) of particular small particle sizes. The invention also relates to a method for the manufacture of the dentifrice in which the capsules are prevented from collapsing or being fractured during mixing with the other dentifrice constituents.

Although the encapsulated flavorings may be employed in tooth powders, dental pastilles, mouth washes, liquid dentifrices and other preparations intended for the cleaning of the mouth and teeth, because the most preferred embodiments of the invention are toothpastes or dental creams which are extrudable from pressurized or flexible containers or tubes, the invention will be described with respect to such embodiments. However, it will be clear to those of skill in the art how to apply such teachings to other forms of dental preparations than the toothpastes being described. Thus, encapsulated flavors may be suspended in thickened liquid dentifrices or may be physically distributed throughout a finely divided tooth powder. Similarly, the manufacturing method herein described may be applied to the making of such other products.

The encapsulated flavors which are used include flavoring agents which may be in solid or liquid form. Most of such agents will be essential oils but the flavors may also include various flavoring aldehydes, esters, alcohols and similar materials, often the higher fatty compounds, known in the art. Examples of the essential oils include oils of spearmint, peppermint, wintergreen, sassafras, clove, sage, eucalyptus, marjoram, cinnamon, lemon, lime, grapefruit and orange. Also useful are such chemicals as methanol, carvone and anethole. Of these, the most commonly employed are the oils of peppermint, spearmint and eucalyptus and anethole, menthol and carvone. In some cases flavorful solvents, such as chloroform and mock chloroforms, may be employed. Such flavorings may be used as liquids or may be solidified by being mixed with a particulate carrier material, such as starch, calcium carbonate, paraffin, vegetable wax, fat, higher fatty acid or other suitable carrier substances. In the cases of solid flavors, such as vanillin, sage, citric acid or licorice, the flavor may be converted to liquid form, if so desired, by dissolving it in the solvent or emulsifying it, usually with the help of a synthetic or natural emulsifying agent. The choice as to whether to utilize particulate solid or liquid flavors or to convert such flavors to a particulate solid or liquid form, respectively, will often depend on the properties desired in the flavor and any other material to be present with it. Thus, where chemical interactions in the capsules are to be avoided it may well be desirable to utilize solid flavors but in those cases where reactions are not probable or objectionable and where quickly detectable strong bursts of flavor are desired as the capsules are broken, liquids may preferably be used. Of course, even in the cases of liquids, the thickness of the liquid may be adjusted by utilization of gelling agents or thickeners, usually to the extent of less than 10% of the flavor, preferably 1 to 10% thereof. Similarly, the sizes of the solid particles within the capsules may be modified. Generally, the flavors will have a viscosity from 0.1 to 1,000 centipoises, preferably about 0.5 to 10 centipoises and the particle sizes will be from 0.1 micron to one millimeter, preferably from 1 to 100 microns in diameters.

The encapsulating material will usually be a substantially water insoluble film-forming compound, preferably a synthetic organic polymeric plastic, when the capsules are to be stored in an aqueous environment. Of such a class of compounds it is preferred to utilize the plastics which are of good tensile strengths so that they are capable of being made into thin walled spheres about a nucleus. Among such polymers are phenol formaldehydes, generally of a 1:1 phenol:formaldehyde ratio; vinyl chloride; polyethylenes; polypropylenes; chlorinated polyvinyl chlorides; polyvinylidene chlorides; polymethaceylates; nylons; polyurethanes; silicones; ABS resins; polyesters and polyethers. Such materials and equivalents of them are described in detail in the conventional handbooks on synthetic organic plastics. For example, see Modern Plastics, Encyclopedia Volume, Vol. 47, No. 10A (1970–1971), at pages 768-787. In addition to the synthetic organic polymers, other water insoluble film forming materials may be employed, such as rubbers; shellacs; hardened or modified gelatins and organic gums; and other resins. The main consideration with respect to the mentioned resins is that they should be capable of being formed into a thin coating about the flavoring agent by use of encapsulation or microencapsulation techniques. Since the methods of encapsulation are known in the art and are not specific parts of the present invention, they will not be described at length herein. However, for the sake of explanation of such methods, reference is made to an article by H. Nack entitled Microencapsulation Techniques, Applications and Problems, appearing in the Journal of the Society of Cosmetic Chemists, Vol. 21, at pages 85-98 (Feb. 4, 1970). In this article there are described various encapsulation processes, of which aqueous phase separation, interfacial polymerization, multi-orifice rotating cylinder, fluidized bed spray coating, melt prilling in a fluidized bed, spray drying diffusional exchange and multiple dispersion techniques are representative. Various other coating techniques known in the art may also be utilized, especially when the capsules are in the larger size portions of the ranges described in the specification. Selection of the process employed will usually depend on the types of flavoring compounds used and their physical states. For example, where a normally liquid conditioning compound is employed, the encapsulation method will usually be different from that used when such a compound is a solid or a plurality of solid particles. Also, if thick coatings are to be made, different techniques may be applied than for thinner or partial coatings. In some cases, secondary films may be produced about the primary coatings on the capsules to strengthen or otherwise affect the capsules. The mentioned article makes evident which method should be employed. In addition to the methods of the articles, other encapsulation processes that are useful are described in the patent literature, of which U.S. Pat. No. Re. 24,899 and German Pat. application No. 1,268,316 may be considered as representative. Instead of the described water insoluble resinous encapsulating materials there may be used for the capsule wall material animal, vegetable, mineral and synthetic waxes, fats, gums or other coatings. Among such compounds are hydrogenated tallows; hydrogenated higher fatty acids, e.g., hydrogenated tallow fatty acids, stearic acid; rosins; paraffinic wases, such as are derived from petroleum hydrocarbons; carnauba wax; Montan wax; and polyoxyethylene waxes, such as those sold as Polawaxes. Higher fatty acid mono, di- and tri-glycerides and higher fatty acid esters of higher fatty alcohols are also useful.

When the medium in which the capsules are dispersed is a non-aqueous one, such as an essentially organic medium in which the normally water soluble compounds do not appreciably or substantially dissolve and in which some of the otherwise useful encapsulating materials dissolve, soften or deteriorate, one may wish to use more hydrophilic encapsulating materials, such as starches, water soluble gums, sodium carboxymethyl cellulose, polyvinyl alcohol, or even inorganic or organic salts. Such materials will be processed in a manner similar to that applicable to the essentially water-insoluble and water- and oil-insoluble encapsulating substances. In some cases it will be desirable to utilize materials which are slightly or significantly soluble in the flavoring compounds or other substances inside the capsules, and also in the eternal medium. Such use will result in products which exhibit variegated coloring or flavoring effects, which may be desirable. However, it will usually be preferred that the encapsulated material be completely or substantially insoluble in both the flavoring compositions and the balance of the dentifrice.

Although capsules of various gross sizes have been utilized, as well as those which are micro-sized, for the purpose of the present invention it will generally be most desirable for the capsule sizes not to be so great as to result in their individual detection by the tongue, teeth or moutn parts. Normally, the capsules will be substantially spherical or of rounded cube shape with a diameter or equivalent diameter in the one micron to 2 millimeters range, preferably in the range of 50 microns to 1 millimeter. An especially desirable range for some applications is from 500 to 800 microns. The thicknesses of the walls of the capsules range from 0.1 micron to 1 millimeter but they are normally in the one to 100 micron range. In some cases, rather than having the encapsulated flavor completely and regularly surrounded by encapsulating material, it may be irregularly and sometimes slightly incompletely covered. Also, while spheres are the most common shapes of the capsules, other shapes may also be utilized.

With the flavoring agent in the capsules there may be present various adjuvants, such as enzymes to facilitate cleaning of plaque from the teeth and breaking down of proteinaceous materials trapped between them; tooth hardening agents; such as stannous fluoride, sodium and potassium monofluorophosphates; calcium fluoride; bactericides, e.g., iodinated nonionic surface active materials, iodinated fats and higher fatty acids, esters and monoglycerides, tetrabromosalicylanilides, hexachlorophene; anti-enzymatic compounds, intended to discourage the formation of plaque on the teeth; and coloring agents, including the conventional F. D. & C. reds, yellows, blues, greens and other colors and mixtures thereof and water-dispersible pigments, e.g., phthalocyanines. Of course, mixtures of such materials may be employed, as may be mixtures of the flavoring agents, carriers, etc. In some cases, emulsifiers or surfae active agents of the types described subsequently may also be present in the materials being encapsulated. It will generally not be necessary to adjust the density of the microcapsulated flavoring agent and/or other materials to maintain them well dispersed in the body of the dentifrice because the viscosity or thickness of the dentifrice is normally sufficient to prevent movement of the capsules except when the dentifrice is being intentionally discharged from a container. Nevertheless, if such density adjustment is considered desirable, as when suspensions of flavoring capsules are in comparatively thin liquid media, adjuvants may be chosen to adjust such density for best suspending of the capsules in the medium. In some cases, minor proportions of air or other gas may be present in the capsules or occluded thereon to maintain the correct density for best suspending effects.

The surface active agent, detergent, or soap present in the dentifrice may sometimes be cationic or amphoteric but will usually be anionic or nonionic. Of these compounds, the anionics are the most preferred. The anionic detergents or surface active agents also usually serve as foaming agents. Such compounds may include long chain fatty or poly-lower alkoxy groups, plus hydrophilic radicals. They will usually be in the forms of salts, especially water soluble salts of alkali or alkaline earth metals. Among the useful anionic detergents may be mentioned the higher fatty acid monoglyceride monosulfates, such as the sodium salts of the monosulfated monoglycerides of hydrogenated coconut oil fatty acid; higher alkyl sulfates, such as sodium lauryl sulfate; higher alkyl aryl sulfonates, such as sodium linear dodecyl benzene sulfonate; higher olefin sulfonates, such as sodium higher olefin sulfonate in which the olefin group is 12 to 21 carbon atoms; higher alkyl potassium sulfoacetates; higher fatty acid esters of 1,2-dihydroxypropane sulfonates, magnesium salt; the substantially saturated higher aliphatic acyl amides of lower aliphatic aminocarboxylic acid alkali metal salts, such as those having 12 to 16 carbon atoms in the fatty acyl radicals, higher alkyl poly-lower alkoxy (of 10 to 100 alkoxies) sodium sulfates; higher fatty acid sodium and potassium soaps of coconut oil and tallow, and the like. As is noted, most frequently the detergents are sulfated or sulfonated compounds, known as sulfuric reaction products. Examples of useful anionic amides which may be employed are N-lauroyl sarcosine and the sodium, potassium and ethanolamine salts of N-lauroyl-, N-myristoyl- and N-palmitoyl sarcosines. In the above descriptions, "higher" refers to chain lengths of 12 to 22 carbon atoms, preferably of 12 to 18 carbon atoms and most preferably of 12 to 16 carbon atoms. Lower means of 2 to 4 carbon atoms, preferably 2 to 3 carbon atoms and most preferably, two carbon atoms. Additional descriptions of such compounds may be found in the text, Surface Active Agents, Vol II (1958), by Schwartz, Perry and Berch.

The nonionic detergents include those containing chains of lower alkylene oxide, e.g., ethylene oxide, propylene oxide, in which there are present from 10 to 100 or more moles of lower alkylene oxide. Among such materials are the block co-polymers of ethylene oxide, propylene oxide and propylene glycol, sold as Pluronics; the alkyl phenyl polyethoxy ethanols, sold as Igepals; the mixed co-polymers of ethylene oxide and propylene oxide, sold as Ucons; and various other well known monionics derived from fatty alcohols or acids and polyethylene oxide. The amphoteric or ampholytic agents and cationics include quaternized imidazole derivatives, such as "Miranols", e.g., miranol $C_2M$; and cationic germicidal detergents, such as diisobutylphenoxyethoxyethyl dimethyl benzyl ammonium chloride; benzyl dimethyl stearyl ammonium chloride; and tertiary amines having a higher fatty alkyl group and two polyoxyethylene groups attached to the nitrogen thereof. Of course, reference to the mentioned text will indicate to one of skill in the art various other suitable surface active detergent and foaming constituents which may be employed in these compositions. Mixtures thereof may be used to adjust the properties to obtain the most desired effect. However, in making such mixtures it will generally be desired to avoid using both anionics and cationics together.

The detergents constitute from 0.5 to 5% of the dentifrice in most cases, although in some instances slightly larger proportions of detergent may be utilized. Rarely, however, will this be greater than 10%. In preferred embodiments of the invention, the detergent content may be decreased to about 1 to 3%. The most preferable detergents utilized are sodium lauryl sulfate or myristyl or palmityl sulfates and sodium N-lauroyl sarcoside, or the myristoyl or palmitoyl compounds. Among highly preferable formulations are those in which mixtures of these two different types of detersive materials are employed. When nonionics are utilized, they will normally be from 0.1 to 3% of the product, preferably from 0.5 to 2% thereof. The amphoterics and cationics can normally be present in proportions less than 2%, preferably less than 1%, but generally more than 0.1%.

The polishing agents are usually finely divided water insoluble powdered materials of particle sizes such that they pass a 140 mesh screen, U. S. Standard Sieve Series. Preferably, they are from 1 to 40 microns, most preferably from 2 to 20 microns in particle sizes, with distribution of particle sizes being normal over the range.

Among the polishing agents that are useful in the preparation of dentrifices may be mentioned dicalcium phosphate, tricalcium phosphate, insoluble sodium metaphosphate, crystalline silica, colloidal silica, complex aluminosilicates, aluminum hydroxide (including alumina trihydrate), magnesium phosphate, magnesium carbonate, calcium carbonate, calcium pyrophosphate, bentonite, talc, calcium silicate, calcium aluminate, aluminum oxide, aluminum silicate, and silica xerogels. In the cases of many of such ionic polishing agents corresponding alkali metal or alkaline earth metal salts, respectively, may be employed. The above listing of polishing agents, and other listings of other constituents of the dentifrice composition to be given in the present specification are not intended to be exhaustive and therefore, for other materials of these types reference should be made to a standard handbook, such as Cosmetics:Science and Technology, by Sagarin, 2nd printing, 1963, published by Interscience Publishers, Inc. Most of the polishing agents mentioned are most useful in the preparation of opaque dentifrices but some of them, such as the colloidal silicas, especially the silica xerogels, and complex sodium aluminosilicates, may be utilized in the manufacture of clear dentifrices, because their indexes of refraction approximate those of the rest of the dentifrice constituents in an appropriate vehicle.

The content of polishing agent in the final dentifrice product is variable, generally being greater for the opaque than for the translucent or transparent dental gels. For example, in the manufacture of commercially acceptable opaque form-retaining, extrudable dental creams there usually will be present 20 to 75% of polishing agent, e.g., dicalcium phosphate, but in the manufature of clear dental gels, also form-retaining and extrudable, the content of polishing agent is typically from 5 to 40%. The preferred proportions of such constituents are 40 to 60% and 10 to 30%, respectively. In the case of the polishing agent for opaque products, a most preferred composition includes hydrated dicalcium phosphate and anhydrous dicalcium phosphate, with the latter being present to the extent of about 5 to 20% of the total dicalcium phosphate content. With respect to the transparent or translucent dental gels, either sodium aluminosilicate complex or silica xerogel will usually be employed separately, although mixtures thereof may find special advantages in some products where the desired polishing properties may be so regulated. It will be seen that the polishing agents utilized in accordance with the invention are normally water insoluble inorganic metal oxides, hydroxides, salts and hydrates but water insoluble organic compounds may also be employed in substitution thereof, although usually for only minor proportions of the total polishing agent. For example, polyacrylamides, polymethyl methacrylates, polyesters and nylons may be utilized.

Of the water insoluble polishing agents, most are well known chemical compounds. The complex aluminosilicate salts, which appear to contain interbonded silica and alumina having Al-O-Si bonds, are described by Tamele, in "Chemistry of the Surface and the Activity of Aluminum-Silica Cracking Catalysts", appearing in Discussions of the Faraday Society, No. 8, pages 270–279 (1950), particularly at page 273, FIG. 1, Curve 3, and in the article by Milliken et al., entitled "The Chemical Characteristics and Structure of Cracking Catalysts", in Discussions of the Faraday Society, No. 8, 279–290 (1950), particularly in the sentence bridging pages 284 and 285. The colloidal silicas used are silica xerogels. Typically, they contain up to about 20% of water, have a refractive index of 1.44 to 1.47 and a loose bulk density of about 0.07 to 0.12 g./c. cm. and are of particle sizes of 1 to 20 microns. Appropriate xerogels have been marketed under the trademarks Syloid 63 and Syloid 74.

The gelling agents used to make the dentifrices of the present invention are known in the art and include the natural and synthetic gums and gum-like materials, such as alkali metal carboxymethyl cellulose, hydroxyethyl carboxymethyl cellulose, polyvinyl pyrrolidone, Irish moss, gum tragacanth, hydroxypropyl methyl cellulose, methyl cellulose, starches, starch glycolates, polyvinyl alcohol, alginates, carob bean gums, and hydrophilic colloidal carboxyvinyl polymers, such as those sold under the trademarks Carbopol 934 and Carbopol 940, diatomaceous earths, bentonite and other natural clays (these also may function as polishing agents, proteinaceous materials, either animal- or vegetable-drived, and synthetic inorganaic clays, such as the silicated clays sold under the trademarks Laponite CP and Laponite SP. Certain colloidal silicas such as the aerogels, Syloids 244 and 266 and Aerosil, and pyrogenic silica, sold as Cab-O-Sils, may be used also for thickening or gelling properties. Of course, as with the other constituents of the dentifrice, mixtures thereof may be employed to obtain specially desirable properties in the product. Generally, the gelling materials utilized are gellable with water or alkanols, especially with polyhydric alcohols, such as glycerol and sorbitol. Usually the gel is formed with at least some water present.

The proportions of gelating agents or thickeners in the present dentifrices are sufficient to form an extrudable, shape-retaining product which can be squeezed from a tube onto a tooth brush and will not fall between the bristles of the brush but rather, will substantially maintain its shape thereon. In almost all cases no more than 10% of gelling agent need be used and in most instances from 0.5 to 10% will suffice, with the preferred range, especially applicable to sodium carboxymethyl cellulose, being from 0.5 to 1.5%.

The liquid vehicle of the dentrifice, together with the gelling agent(s) and other constituents, forms an extrudable mass of a non-dripping consistency when extruded from a collapsible tube, such as an aluminum or lead tube. Thus, by the addition of more vehicle, the dental cream can be thinned and conversely, by the addition of more solids, especially more gelling agents, the products can be thickened. In most dentifrices the liquid portion comprises water, glycerine and sorbitol, with the last usually being added in aqueous solution, or various suitable mixtures thereof. In the present description the vehicle will be considered as distinct from the water. Although it is preferred to employ mixtures of glycerol and sorbitol, other suitable vehicles may also be present, either with the mentioned polyhydric alcohols or in replacement for them. Thus, propylene glycol, polyethylene glycol, mannitol and polypropylene glycol may be employed, providing that they are physiologically acceptable and produce products having a desired refractive index, in the case of manufacture of visually clear dentifrices. Normally, the proportion of vehicle is determined by the physical properties of the extrudate. Usually, however, from about 10 to 90% of the vehicle will be employed, with from 10 to 35% being a typical range for production of opaque dentifrices and from 40 to 90% being useful for the manufacture of clear dental preparations. Preferred ranges are, respectively, from 15 to 30% of the polyhydric alcohols for the opaque dentifrices and from 50 to 75% in the clear products. In the opaque products it is preferred that the glycerol:sorbitol ratio, if both these polyhydric alcohols are present, should be from 0.3:1 to 10:1 and in the clear products from 1:5 to 5:1, more preferably from 1:3 to 1:1.

The water content of the product, including free water present with the sorbitol solution, in the synthetic detergent mixture and in any other constituents, often is greater for the opaque products than for the clear products. Thus, for the opaque dentifrices the water content may range from 5 to 35% but will usually be about 8 to 30%, preferably from 20 to 30%. With respect to the clear dentifrices, this range may be from 0 to 30% but will normally be from 10 to 20%, most usually about 15 to 20%. The water employed will preferably be deionized water and usually is irradiated with ultraviolet light to assure sterility of the product. In a similar manner, if considered important, the entire product may similarly be irradiated while being mixed, degassed or otherwise processed, so as to decrease bacterial counts. The polishing agents utilized in accordance with this invention are normally water insoluble.

The encapsulated flavoring material will usually be a minor proportion of the dentifrice product, preferably from 0.1 or 0.5 to 10% thereof. Of the encapsulated particles, a major portion, preferably from 60 to 99% will be of the encapsulating material, although, especially when diluents or carriers for the flavoring are employed, as little as 10% may be used. In the most preferred embodiments, the proportion of encapsulating material will be from 70 to 90%. In those instances where carriers or diluents are used, they may usually amount to from 1 to 10 times the amount of actual encapsulated flavor employed. Of course, the percentages of adjuvants or other materials also present may be regulated for best results and usually will be from 0.2 to 5 times the weight of the flavoring in the capsules. The proportion of flavoring in the dentifrice external to the encapsulated parts thereof will normally be from 0.1 to 2% of the entire product, preferably from 0.5 to 1.5% thereof, Normally, more of the flavoring will be in encapsulated form than will be evenly distributed throughout the dentifrice. However, it is desirable for the "background" flavoring of the dentifrice to be mild so that when the capsules are broken or dissolved in use the releases of flavor will be very apparent to the user as "bursts" of flavor and will not be overpowered by the background flavor. Similar effects may be obtained with color instead of flavor being the material released. Because the mouth is a substantially aqueous environment the flavors utilized will normally be water soluble, emulsifiable or dispersible. The encapsulating material, and often the dentifrice base, will be chosen accordingly so as to be substantially impenetrable by the flavor although, in some instances, a controlled leaching of coloring or other adjuvant may be intentionally produced. By "substantially impenetrable" it is meant that over 80% and preferably over 90% of the flavoring remains in the microcapsules until the time of intended use.

To make the present dentifrice or oral products is a comparatively simple matter, once the capsules have been produced. Various methods of making the capsules have already been described and any of these may be applicable. However, to limit penetration of the capsule wall, when water soluble flavorings are employed it may be desirable to mix them with more lipophilic bases before encapsulation.

After the production of the encapsulated flavor and/or other materials it is a simple matter to blend them in with the rest of the dentifrice constituents at a suitable point in the manufacturing procedure. In most cases, air or other gases will be removed from the dentifrice during manufacturing and such degassing will often be assisted by application of heat. In such an operation, the viscosity of the dentifrice will be diminished so that the stains of mixing will not tend as readily to break the capsule walls. Accordingly, the flavor capsules will normally be added near the end of the mixing operation, when the viscosity of the dentifrice is lowered, usually having had air or other gases removed from it and having had its temperature raised. Then, after mixing is completed, the temperature will be lowered to about ambient, usually after filling of dentifrice into dispensing tubes or other containers. In preferred embodiments of the invention the encapsulated flavors will be degassed before blending with the other dentifrice constituents, such degassing normally taking place at an absolute pressure of between about 1 and 260 millimeters of mercury over a period of 30 seconds to five minutes. The degassing of the flavor capsules is especially useful because it helps to remove occluded air and thereby improves the appearance and properties of the product, especially if it is of the clear gel type. The temperature to which the dentifrice is raised during mixing may be from 30 to 60°C., preferably from 40° to 50°C., and the mixing time will be from 30 seconds to 10 minutes. The viscosity of the dentifrice mixture at the time of blending the flavor capsules with the balance of the composition will usually be less than 70% of that at normal ambient conditions and will preferably be less than 50% of such "viscosity". A range of apparent viscosities during mixing may be in the area of 100 to 100,000 centipoises but the important consideration is that it will be less than would have been the case had the viscosity of the dentifrice not intentionally been diminished to promote ready mixing of the encapsulated flavor without destruction of the capsules during mixing operations. Of course, mixing means will be employed which will not crush the capsules and which operate at a low enough speed and with great enough clearances so as not to destroy the encapsulating sheel material.

Advantages obtained by the mixing technique described are significant because they result in more available encapsulated flavor in the final product than would otherwise be the case. Thus, the flavor bursts or signals as the capsules are broken during use of the dentifrice result in release of more flavoring and stronger signals. Incidentally, sweetening agents are contemplated as part of the flavors described herein. When various normally incompatible materials are encapsulated in the dentifrice the maintenance of the integrity of the capsule walls prevents undesired reactions taking place in the dentifrice matrix. Also, when different thicknesses of capsule material are used, the mixing at low viscosity prevents the thinnest of these from being broken prematurely. Another advantage of the invention is that when the dentifrice is squeezed from the tube fresh flavor is released as the capsules on the surface are broken by shearing contacts with the tube neck interior walls, given off a fresh and pleasant aroma of the flavoring at the moment of use.

The following examples illustrate the invention but do not limit it. All parts are by weight and all temperatures are in °C.

EXAMPLE 1

A spearmint flavoring is encapsulated in substantially spearmint-impenetrable shells or coatings of a variety of encapsulating materials, including 1) polyvinyl chloride; 2) polyethylene; 3) phenol-formaldehyde; 4) paraffin; 5) carob bean gum; 6) shellac; and 7) hardened gelatin. The microcapsules are of sizes distributed over the range of 50 microns to one millimeter, distribution being substantially normal. In other cases the distribution is controlled so that the particle sizes are in the 500 to 800 micron range. Capsule wall thicknesses are assorted through the 1 to 100 micron range, averaging about 50 microns. The proportion of spearmint flavoring in the microcapsule is about 30% and present with the spearmint is about 10% of sweetener (sodium saccharin), 2% of green colorant (F. D. & C. Green) of the water soluble type, and 10% of a soluble fluorophosphate, sodium salt. All such percentages are based on the spearmint. In some instances, wherein penetrability of the flavor and color are to be minimized, the various "internal" ingredients of the microcapsules are mixed with paraffin wax (25% of the ingredients) before encapsulation.

After preparation of the microcapsules, they are degassed by subjection to a vacuum (40 mm. Hg absolute pressure) for five minutes and are then blended with a dental cream of the following formula, made as described.

|  | Parts |
| --- | --- |
| Glycerine (99%, C.P.) | 7.0 |
| Sorbitol (70% aqueous solution) | 12.0 |
| Sodium saccharin | 0.1 |
| Preservative | 0.5 |
| Gelling agent (sodium carboxymethyl cellulose) | 1.0 |
| Water (irradiated tap) | 19.0 |
| Tetrasodium pyrophosphate | 0.5 |
| Water (irradiated tap) | 1.2 |
| Dicalcium phosphate SM (Albright and Wilson) | 38.0 |
| Calcium carbonate (precipitated, dense) | 10.0 |
| Sodium N-lauroyl sarcosine solution (25% aqueous) | 9.5 |
| Spearmint flavor (essential oil of spearmint) | 0.3 |

The solution of vehicles is made, subjected to the vacuum described for the encapsulated flavor and the mixture of flavor, preservative and gelling agent, in the 19 parts of irradiated tap water is prepared and subjected to degassing by the same technique. Subsequently, the pyrophosphate solution is made in 1.2 parts of the tap water and is blended with the previous aqueous suspension and the mixture of vehicles. The temperature is elevated to 45°C., while the mixture is being degassed at about 40 mm. Hg absolute pressure over 10 minutes. Then, the polishing agent and detergent solution are added, after preliminary degassing. The temperature is maintained about 45°C. and 2.5 parts of the encapsulated flavoring (and other ingredients) are mixed in, taking care not to have the viscosity over about 40,000 centipoises and making sure that the mixer (Dopp) clearances are such that the microcapsules are not broken. After about ten minutes mixing, with application of vacuum and maintenance of elevated temperature, the dentifrice preparation is considered to be complete and it is packed into tubes in conventional manner. The tubes are then sent to storage and cooled to ambient temperature, at which the viscosity of the product increases to about 100,000 centipoises.

The product analyzes about 8% glycerine, 8.4% sorbitol, 2% sodium N-lauroyl sarcosine, 35% moisture and 48% alcohol insolubles. Its apparent specific gravity is about 1.52 and its pH is about 7.7.

Upon subsequent use, when the product is squeezed from the tube and placed on a toothbrush, there is a distinct fresh spearmint fragrance apparently resulting from fracturing of some of the microcapsules. Also, on use, the spearmint flavor is released from the microcapsules, as is the coloring, by contact with the toothbrush, teeth and mouth, to reinforce both the flavoring and coloring of the product. Some of the coloring, a small proportion thereof, leaches through the capsule walls on storage and lightly colors the product but the subsequent coloring from the ruptured microcapsules and the increase in flavor resulting when the user fractures the capsule walls by brushing the teeth with the dentifrice are significantly noticeable as bursts of flavor and color and indicate to the user by taste and appearance when brushing has been vigorous enough and may be terminated.

In variations of the formula, in which the various encapsulating materials mentioned herein are employed with the basic formula, the same results are noted. The capsules are small enough so that they are not of objectionable size or feel during use of the dentifrice. Because the dentifrice is not swallowed, and because the encapsulating material employed in small quantities, the use thereof is found to be harmless.

In other experiments modeled after that reported above, when special efforts are not made to prevent crushing of the capsules during mixing there is a noticeable decrease in the effectiveness of the flavor release from the capsules during use of the dentifrice. However, when such procedures are followed and when various flavors and mixtures of flavors are employed, such as spearmint or peppermint in thicker walled capsules and cherry flavoring in thinner walled capsules, with the proportions thereof being about 50:50, both flavors and distinctively produced, the cherry during the earlier part of brushing and the spearmint or peppermint later on, signalling the end of the brushing operation.

In other experiments the capsules made are suspended in clear gel dentifrices, wherein the coloring materials are apparent, giving the clear gels a distinctive colored appearance. Instead of utilizing clear gels with suspended polishing agents in them, the capsules are also suspended in thickened liquid detergents, based on sodium lauryl sulfate and sodium carboxymethyl cellulose, wherein they serve to release coloring and flavoring until the cleaning operation is complete.

In other experiments, the flavor(s) in the capsules are changed to eucalyptus, anethole, menthol and carvone and the proportions are varied over 0.5 to 5% range, with similar results. Generally, however, the total amount of flavoring employed will be from about 0.5 to 2% for best taste effects.

EXAMPLE 2

| | Parts |
|---|---|
| Glycerine (99.5% C.P.) | 17.0 |
| Hydroxyethyl cellulose | 1.0 |
| Sodium saccharin | 0.2 |
| Deionized water, irradiated | 14.5 |
| Hydrated alumina (2 to 20 microns in dia.) | 55.0 |
| Sodium N-lauroyl sarcosine | 2.0 |
| Glycerine (99.5% C.P.) | 2.9 |
| Deionized water, irradiated | 4.6 |
| Dental cream flavoring (essential oils, sweeteners, esters) | 0.4 |

The above opaque dental cream is made by a method corresponding to that of Example 1, wherein the various portions of the formulation are degassed under vacuum and are subsequently heated to a temperature of about 50°C., before blending in with the base of encapsulated flavors. The hydroxyethyl cellulose is dissolved or dispersed in the glycerine and vacuum is applied, according to the method of Example 1. At the same time, an aqueous solution of the saccharine is made in the deionized water, following which it is degassed, and degassed hydrated alumina is blended with a mixture of the glycerine, hydroxyethyl cellulose, saccharine and water. Then the temperature is raised and a previous mixture of water, glycerine and sodium N-lauroyl sarcosine (in proportions of about 4.6:2.9:2.0), degassed by the described method, is mixed in. Usual dental cream manufacturing equipment is employed.

After the preparation of the base, at an elevated temperature, a peppermint flavor, encapsulated in hardened gelatin and/or phenol-formaldehyde resin and having particle sizes in the 500 to 800 micron diameter range, with wall thicknesses of about 50 to 150 microns is blended in with the dentifrice, with care being taken to avoid fracturing the capsules. Proportions of the capsules employed are 1, 2 and 5%, with the flavor accounting for about 30% of the total capsule weight. Use of the lower percentage does not result in as good a series of flavor bursts as those obtainable by use of the higher percentages, although at 5% the flavor is considered to be too strong by some.

In actual use, the release of flavor and subsequent halting of any further release of flavor are utilized to indicate when teeth have been brushed sufficiently. This normally takes about one to two minutes.

EXAMPLE 3

The procedure of Example 2 is followed, utilizing the formula given below, to make a clear gel dentifrice.

| | Parts |
|---|---|
| Sorbitol (70% aqueous solution) | 44.7 |
| Laponite CP (Laporte) | 2.0 |
| Coloring solution | 0.1 |
| Synthetic glycerine (99.3%) | 17.0 |
| Deionized water | 3.0 |
| Sodium aluminum silicate AS-8 (Degussa) | 16.0 |
| Syloid 244 (thickener) | 5.0 |
| Flavor (cinnamon) | 0.4 |
| Synthetic glycerine (99.3%) | 8.0 |
| Sodium N-lauroyl sarcoside and/or sodium lauryl sulfate | 2.0 |
| Sodium saccharin | 0.15 |

The various parts of the formulation are blended together and subjected to vacuum treatment and heat, in the manner described with respect to the preceding examples, after which the encapsulated flavoring is added. The proportion of encapsulated flavoring added corresponds to about 3%, of which about 15% is active flavoring normally used for commercial dentifrices. The encapsulating agents are those described in Example 1.

The product resulting is of excellent clarity and taste and the microcapsules of flavor, when they have coloring materials such as F. D. & C. Red added to them, to the extent of 10% of the flavor, give a product a distinctive appearance. The specific gravity of the product is about 1.37 and its pH is about 8.8. The bursts of flavor released during use indicate that brushing should continue until they cease, which usually takes about one or one and a half minutes. The residues of the capsules are essentially impalpable and are not found to be objectionable by users of the dentifrice.

The invention has been described with respect to various examples thereof but it is clear that such examples and previously given illustrations are not limitative, since one of ordinary skill in the art will be able to employ substitutes and equivalents without departing from the inventive concept.

What is claimed is:

1. A dentifrice adapted to release a plural flavor burst signalling the onset of and the completion of a toothbrushing operation, respectively, comprising essential oils of distinctive non-minty flavor in thin walled microcapsules producing a distinctive initial non-minty flavor during early brushing of the teeth, and essential oils of mint flavor in a thicker walled microcapsule than said thinner walled microcapsule and producing a mint flavor subsequent to said non-mint flavor and signalling the onset of the completion of the brushing operation, said nonminty flavor released initially from said thin walled microcapsules when said dentifrice is extruded from a container by shearing contact with the container neck wall and by rupture on contact with the teeth, the mint flavor in said thicker walled microcapsules being adapted to signal the onset of completion of said brushing operation by being ruptured during the course of brushing the teeth, said flavors encapsulated by 30% of the total capsule weight in a water insoluble, film forming synthetic organic polymeric plastic having an equivalent diameter of about one micron to 2 millimeters and having a wall thickness of about 0.1 micron to 2 millimeters, included in a concentration of about 0.1 to 10% into an unflavored dentifrice having a viscosity of under about 40,000 cps.

2. A dentifrice as defined in claim 1 wherein said flavoring oils remain substantially encapsulated in said microscapsule during storage.

3. A dentifrice as defined in claim 1 wherein said microcapsules additionally contain at least one coloring material.

4. A dentifrice as defined in claim 3 wherein said microcapsules contain differing coloring materials.

5. A dentifrice as defined in claim 4 wherein said shearing contact results in a mottled color of differing intensity.

6. A dentifrice as defined in claim 1 wherein the walls of like microcapsules have a substantially uniform thickness thereby producing a substantially even release of flavor.

7. A dentifrice as defined in claim 1 which is a toothpaste comprising a polishing agent, a vehicle for the polishing agent and a dentifrice flavoring agent in said vehicle.

8. A dentifrice as defined in claim 7 wherein the rupture of said microcapsules produces a color change in contrast to the color of said vehicle.

9. A dentifrice as defined in claim 7 which further includes about 0.5 to 10% jelling agent and about 0.5 to 5% of a synthetic organic or soap detergent, said polishing agent being selected from the group consisting of sodium aluminum silicate, hydrated alumina, dicalcium phosphate, silica aerogel, calcium carbonate and suitable mixtures thereof, said vehicle being selected from the group consisting of sorbitol, glycerole, water and suitable mixtures thereof, said gelling agent being selected from the group consisting of sodium carboxymethyl cellulose, hydroxyethyl cellulose, polyvinyl alcohol, Irish Moss, silica aerogel and suitable mixtures thereof, sand detergent being selected from the group consisting of water soluble higher fatty acid soaps and synthetic anionic and nonionic detergents.

10. A dentifrice as defined in claim 7 additionally containing about 0.1 to 2% flavoring material homogeniously dispersed in said vehicle.

11. A dentifrice as defined in claim 1 wherein said capsules additionally contain a material selected from the group consisting of coloring agents, enzymes, bacteriacides and antienzymatic compounds.

12. A dentifrice as defined in claim 7 in clear gel form containing a polishing agent of approximately the same index of refraction as the balance of the dentifrice apart from the encapsulated portion.

13. A dentifrice as defined in claim 1 wherein said flavors are selected from the group consisting of peppermint, spearmint, anethole, menthol, carvone, eucalyptus, cinnamon, cherry, wintergreen, sassafras, clove, sage, marjoram, lemon, lime, grapefruit, orange and suitable mixtures thereof.

14. A method of brushing the teeth whereby plural flavor burst is produced, comprising contacting said teeth with a dentifrice as defined in claim 1.

15. A dentifrice as defined in claim 1 wherein said polymer is selected from the group consisting of polyethylene, polypropylene, polymethacrylate, polyurethane, nylon, silicone, polyester, polyether, acrylonitrile - buyadiene-styrene, phenol-formaldehyde and suitable mixtures thereof.

16. A dentifrice as defined in claim 15 wherein said phenol-formaldehyde is employed in about a 1:1 ratio.

17. A dentifrice according to claim 1 wherein said thinner walled capsule contain a fruit flavor.

18. A dentifrice as defined in claim 16 wherein the proportion of thicker walled capsules to thinner walled capsule is about 50:50.

19. A dentifrice as defined in claim 1 wherein said thinner walled capsules have a thickness of about 50 microns and said thicker walled capsule about 150 microns.

* * * * *

UNITED STATES PATENT OFFICE
CERTIFICATE OF CORRECTION

Patent No. 3,957,964     Dated May 18, 1976

Inventor(s) John Edward Grimm III

It is certified that error appears in the above-identified patent and that said Letters Patent are hereby corrected as shown below:

1. A dentifrice adapted to release a plural flavor burst signalling the onset of and the completion of a toothbrushing operation, respectively, comprising essential oils of distinctive non-minty flavor in thin walled microcapsules producing a distinctive initial non-minty flavor during early brushing of the teeth, and essential oils of mint flavor in a thicker walled microcapsule than said thinner walled microcapsule and producing a mint flavor subsequent to said non-mint flavor and signalling the onset of the completion of the brushing operation, said nonminty flavor released initially from said thin walled microcapsule when said dentifrice is extruded from a container by shearing contact with the container neck wall and by rupture on contact with the teeth, the mint flavor in said thicker walled microcapsules being adapted to signal the onset of completion of said brushing operation by being ruptured during the course of brushing the teeth, said flavors encapsulated by 30% of the total capsule weight in a water insoluble, film forming synthetic organic polymeric plastic having an equivalent diameter of about one micron to 2 millimeters and having a wall thickness of about 0.1 micron to [2] 1.0 millimeters, included in a concentration of about 0.1 to 10% into an unflavored dentifrice having a viscosity of under about 40,000 cps.

Signed and Sealed this

Second Day of November 1976

[SEAL]

Attest:

RUTH C. MASON
Attesting Officer

C. MARSHALL DANN
Commissioner of Patents and Trademarks